United States Patent
Muta et al.

(10) Patent No.: US 8,974,923 B2
(45) Date of Patent: Mar. 10, 2015

(54) ORGANIC COMPOUND AND ORGANIC LIGHT-EMITTING DEVICE HAVING THE SAME

(75) Inventors: Hajime Muta, Zama (JP); Takeshi Sekiguchi, Tokyo (JP); Ryuji Ishii, Yokohama (JP); Koichi Suzuki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 228 days.

(21) Appl. No.: 13/583,731

(22) PCT Filed: Mar. 14, 2011

(86) PCT No.: PCT/JP2011/056669
§ 371 (c)(1),
(2), (4) Date: Sep. 10, 2012

(87) PCT Pub. No.: WO2011/122381
PCT Pub. Date: Oct. 6, 2011

(65) Prior Publication Data
US 2013/0001537 A1    Jan. 3, 2013

(30) Foreign Application Priority Data
Mar. 31, 2010    (JP) .................................. 2010-082828

(51) Int. Cl.
C07D 403/04    (2006.01)
H01L 27/32    (2006.01)
H01L 51/54    (2006.01)
C09K 11/06    (2006.01)
H01L 51/00    (2006.01)
H05B 33/14    (2006.01)

(52) U.S. Cl.
CPC .............. *C07D 403/04* (2013.01); *C09K 11/06* (2013.01); *H01L 51/0072* (2013.01); *H05B 33/14* (2013.01); *C09K 2211/1029* (2013.01); *C09K 2211/1044* (2013.01); *H01L 51/0058* (2013.01); *H01L 51/0085* (2013.01)
USPC ............................................. 428/690; 257/40

(58) Field of Classification Search
None
See application file for complete search history.

(56) References Cited

FOREIGN PATENT DOCUMENTS

| | | |
|---|---|---|
| JP | 2004-288439 A | 10/2004 |
| JP | 2005-154412 A | 6/2005 |
| JP | 2007-126439 A | 5/2007 |
| JP | 2007-180147 A | 7/2007 |
| JP | 2009-057307 A | 3/2009 |
| JP | 2009-120582 A | 6/2009 |

OTHER PUBLICATIONS

Subrayan et al., "Syntheses and characterization of aromatic secondary and tertiary amines and a new imidazolone from dicyanoimidazole", Dept. of Chemistry, The University of Michigan, vol. 51, No. 22, p. 6167-6178.

Voverman et al., "Preparation of substituted 2-pyridones by thermal rearrangement of propargylic pseudoureas", Org. Chem. 1981,46,811-813.

*Primary Examiner* — J. L. Yang
(74) *Attorney, Agent, or Firm* — Canon U.S.A., Inc. IP Division

(57) ABSTRACT

The present invention provides a novel organic compound that is chemically stable and can be used as a host material for phosphorescence emission.

The present invention provides a benzimidazolyl carbazole compound shown by Formula [1] described in the description.

8 Claims, 1 Drawing Sheet

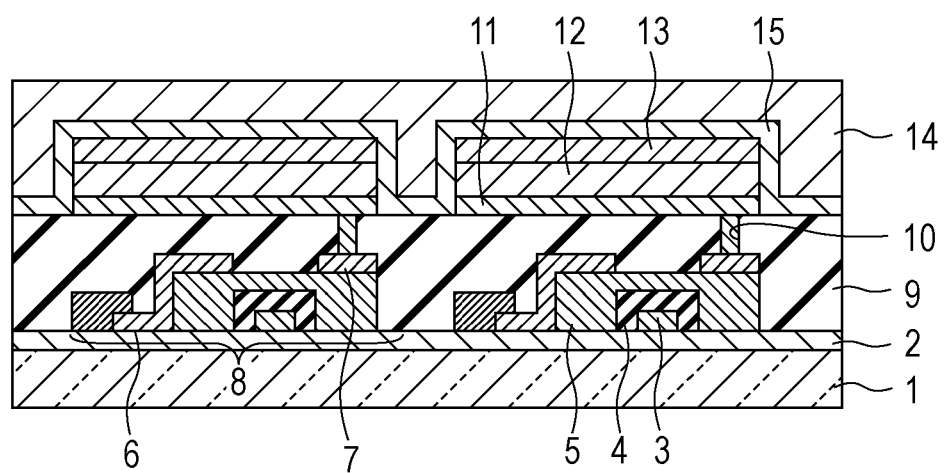

ORGANIC COMPOUND AND ORGANIC LIGHT-EMITTING DEVICE HAVING THE SAME

TECHNICAL FIELD

The present invention relates to a benzimidazolyl carbazole compound, which is a novel organic compound, and relates to an organic light-emitting device having the novel compound.

BACKGROUND ART

An organic light-emitting device has a structure in which two electrodes opposing each other and organic compound layers including a light-emitting layer disposed between these electrodes are layered on a transparent substrate. In the organic light-emitting device, holes and electrons supplied from the electrodes by application of a voltage between the electrodes recombine in the light-emitting layer to generate excitons and give emission of light from the excitons.

The organic light-emitting devices have attracted attention as a technology of the next generation for full color displays having fast response, high luminous efficiency, and flexibility, and material technologies and device technologies for the organic light-emitting devices have been vigorously developed. Among the organic light-emitting devices, in particular, a device utilizing electroluminescence is called an organic electroluminescent (EL) device in some cases.

Recently, in order to enhance the luminous efficiency, organic light-emitting devices employing a system in which phosphorescence through triplet excitons is utilized (hereinafter such organic light-emitting devices are referred to as phosphorescent devices) have been actively developed.

A system in which fluorescence through singlet excitons is utilized is also used, but, in such a system, in principle, only 25% of the excitons generated by recombination of holes and electrons may be used for light emission. On the other hand, in the light emission through triplet excitons, 100% of the excitons may be used for light emission, thus, the luminous efficiency is high.

As light-emitting materials, metal complexes containing iridium (Ir), such as (2-carboxypyridyl)bis(3,5-difluoro-2-(2-pyridyl)phenyl)iridium (FIrpic), are widely used from the viewpoints of material stability and luminous efficiency.

Recently, in addition to luminous efficiency, from the viewpoints of environmental protection and energy saving, a demand for reducing the power consumption of, in particular, displays has been increasing, and development for organic light-emitting devices that are driven by low voltages has been conducted for realizing low-voltage driving of displays.

Furthermore, in the phosphorescent devices, since the device performance is highly influenced by the performance of a host material used together with a light-emitting material (guest material) in the light-emitting layer, the host material has been actively developed.

In order to simultaneously achieving an increase in luminous efficiency and a reduction in voltage of a phosphorescent device, it is necessary that the host material to be used has triplet energy higher than that of the light-emitting material and has high ability of transporting both holes and electrons responsible for excitons to generate light emission. However, as matters now stand, known host materials have not arrived at sufficiently practical levels.

In particular, in blue phosphorescent devices, since the emission peak wavelength of the light-emitting material is short, 450 to 470 nm, the host material is required to have triplet energy higher than that of such a light-emitting material. However, a material that satisfies these strict requirements and has arrived at a practical level has not been found yet.

PTL 1 discloses a compound in which the nitrogen atom of carbazole is substituted with a phenyl group. This carbazole compound has high triplet energy and a high hole-transporting property, but its electron-transporting property is not so high compared to its hole-transporting property. Therefore, the carbazole compound is insufficient for a reduction in voltage.

PTL 2 discloses a device in which a benzimidazole compound is used in the light-emitting layer. However, since the compound disclosed in PTL 2 is not a compound having high triplet energy, when the compound is used in a phosphorescent device, an improvement in luminous efficiency and a reduction in voltage are not achieved.

CITATION LIST

Patent Literature

PTL 1 Japanese Patent Laid-Open No. 2005-154412
PTL 2 Japanese Patent Laid-Open No. 2004-288439

SUMMARY OF INVENTION

Technical Problem

The present invention provides a novel organic compound and also provides an organic light-emitting device that has a high luminous efficiency and can be driven by a low voltage.

Solution to Problem

The novel organic compound according to the present invention is a benzimidazolyl carbazole compound shown by the following Formula [1].

[Chem. 1]

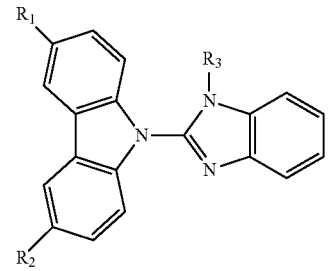

[1]

In the formula, $R_1$ and $R_2$ each independently represent an unsubstituted phenyl group or a substituted phenyl group substituted with an alkyl group having 1 to 6 carbon atoms; and $R_3$ represents an alkyl group having 1 to 6 carbon atoms.

Furthermore, the organic light-emitting device of the present invention is an organic light-emitting device having at least one organic layer disposed between a pair of electrodes opposing each other, wherein the at least one organic layer includes a light-emitting layer containing a benzimidazolyl carbazole compound shown by Formula [1].

Advantageous Effects of Invention

According to the present invention, a novel compound useful as a host material of a phosphorescent device is provided. Furthermore, an organic light-emitting device that has a high luminous efficiency and can be driven by a low voltage is provided.

BRIEF DESCRIPTION OF DRAWINGS

FIG. 1 is a schematic view illustrating a cross-sectional structure of an organic light-emitting device and a switching device connected thereto.

DESCRIPTION OF EMBODIMENT

The novel organic compound according to the present invention is a benzimidazolyl carbazole compound shown by the following Formula [1].

[Chem. 2]

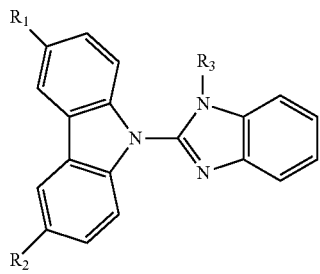

[1]

In the formula, $R_1$ and $R_2$ each independently represent an unsubstituted phenyl group or a substituted phenyl group substituted with an alkyl group having 1 to 6 carbon atoms; and $R_3$ represents an alkyl group having 1 to 6 carbon atoms.

$R_1$ and $R_2$ each independently are an unsubstituted phenyl group or a substituted phenyl group substituted with an alkyl group having 1 to 6 carbon atoms. This can maintain the lowest triplet energy to a high level. In particular, $R_1$ and $R_2$ can each independently be a tolyl group, a xylyl group, or a mesityl group.

In the compound shown by Formula [1] of the present invention, benzimidazole is bonded to the nitrogen atom of carbazole at the position of the benzimidazole shown by Formula [1]. This allows simultaneous achievement of high triplet energy and an improvement in electron-transporting property.

Accordingly, the benzimidazolyl carbazole compound according to the present invention can be used as a host material for an Ir metal complex that emits blue light having a short emission peak wavelength.

Specific examples of the benzimidazolyl carbazole compound according to the present invention are shown below, but the present invention is not limited thereto.

[Chem. 3]

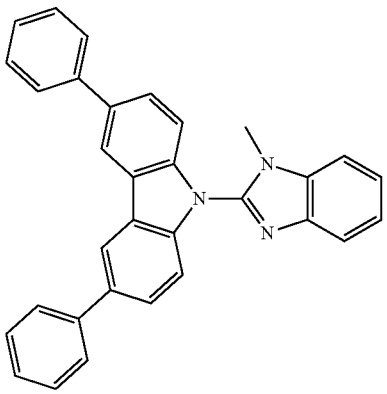
H-01

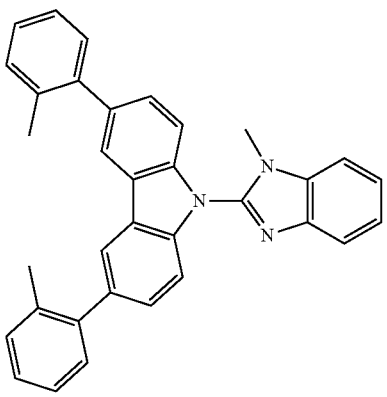
H-02

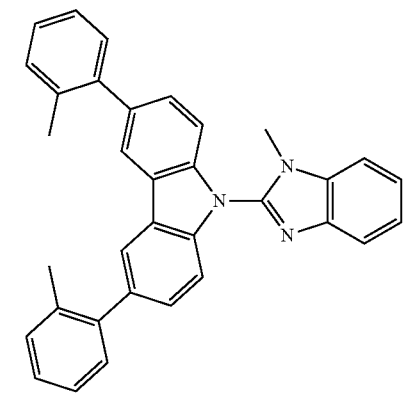
H-03

[Chem. 4]

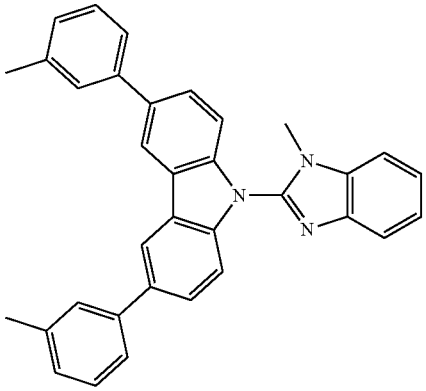
H-04

H-05
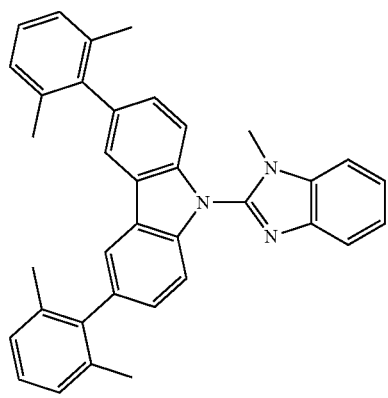
H-06
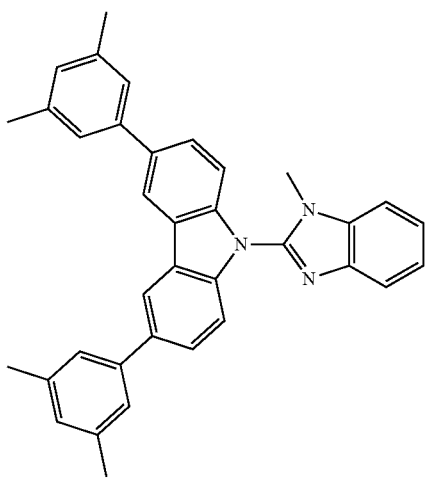
[Chem. 5]
H-07
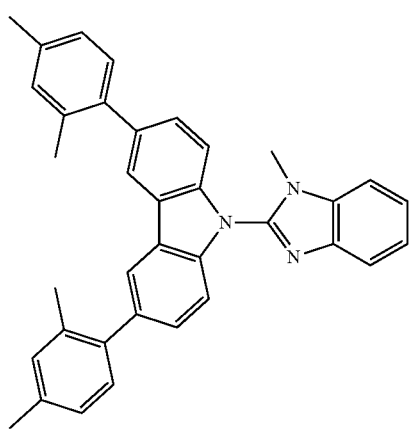
H-08
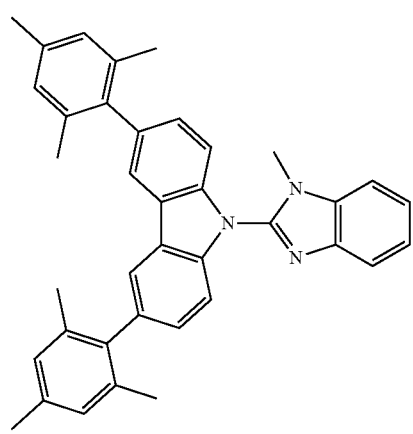
H-09
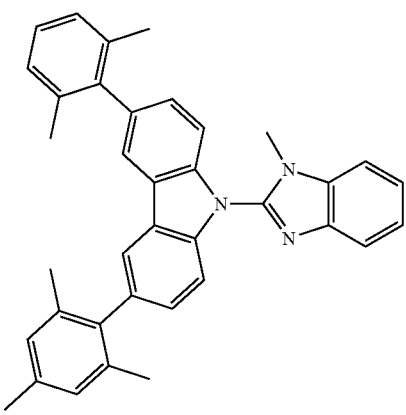
[Chem. 6]
H-10
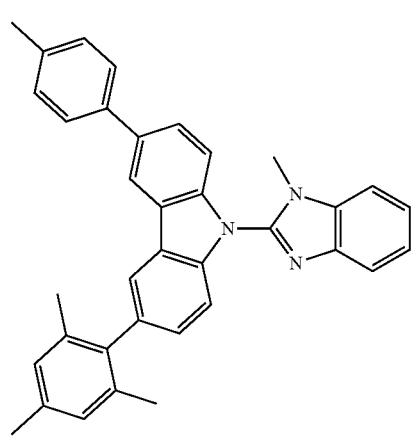

H-11
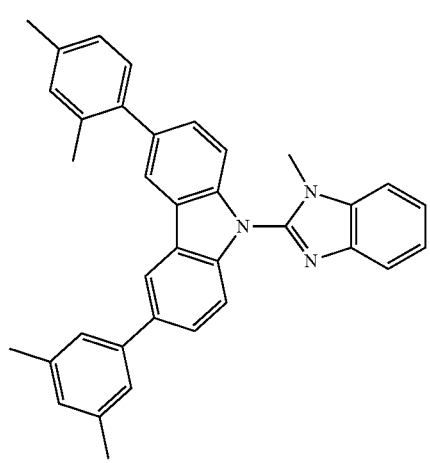
H-12
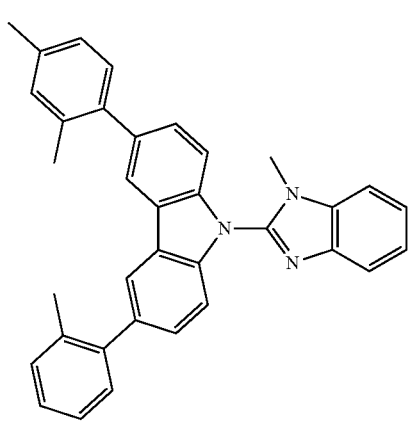
[Chem. 7]
H-13
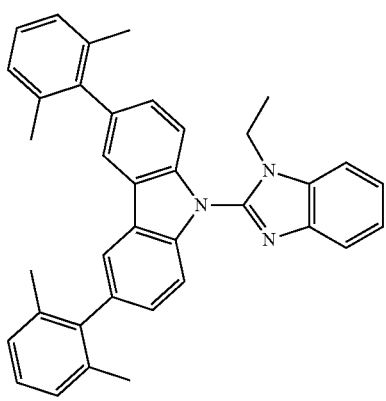
H-14
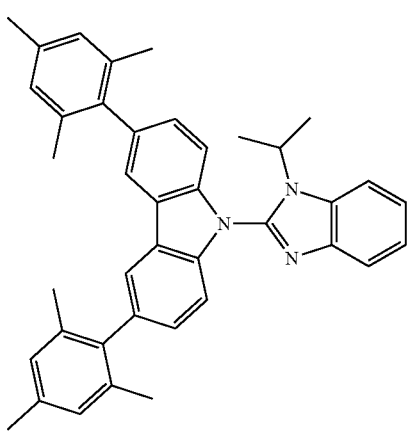
H-15
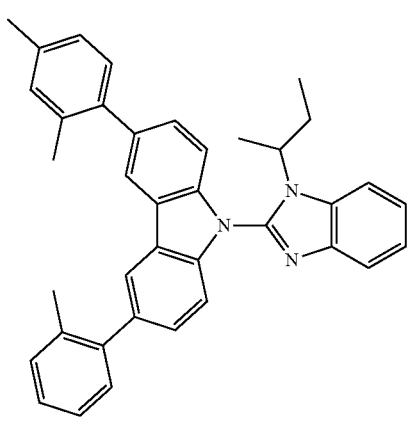
[Chem. 8]
H-16
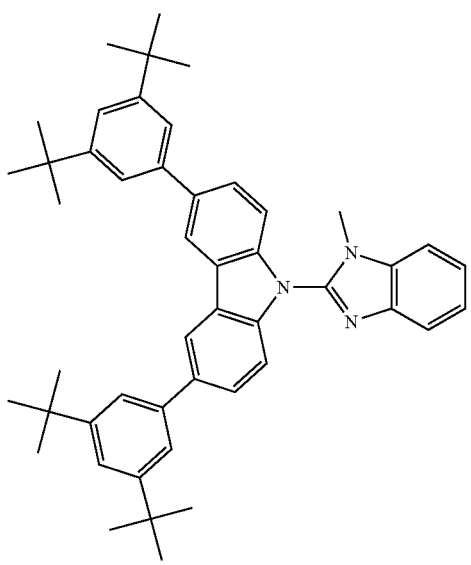

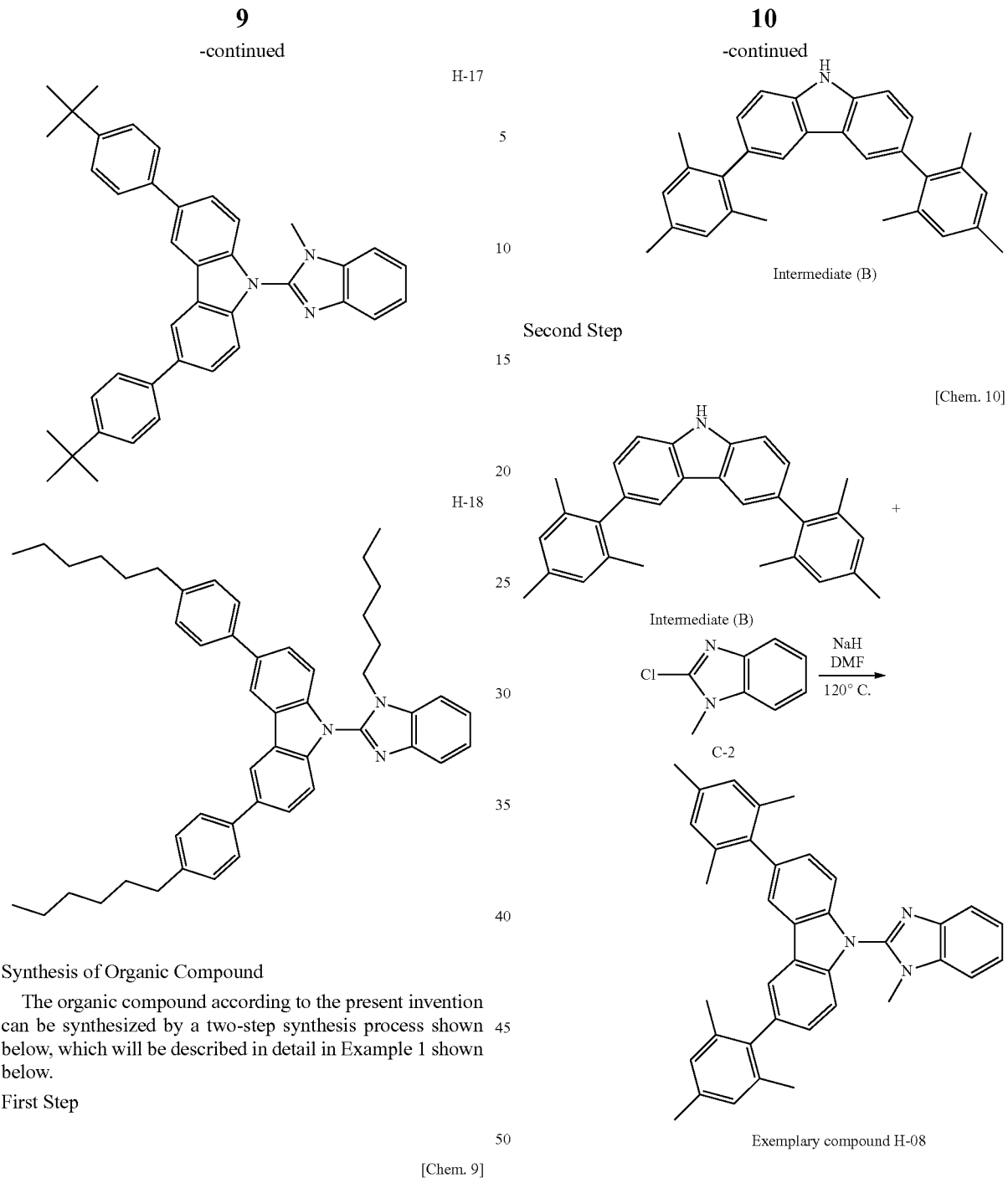

Synthesis of Organic Compound

The organic compound according to the present invention can be synthesized by a two-step synthesis process shown below, which will be described in detail in Example 1 shown below.

First Step

The benzimidazolyl carbazole compounds of the present invention, for example, the above-mentioned compounds, can be each synthesized by changing the starting material A-2 in the first step or the intermediate C-2 in the second step.

Description of Organic Light-Emitting Device

An organic light-emitting device according to the embodiment will now be described.

The organic light-emitting device according to the embodiment has at least one organic layer disposed between a pair of electrodes opposing each other, wherein the at least one organic layer includes a light-emitting layer containing a benzimidazolyl carbazole compound shown by the above-mentioned Formula [1].

The present inventors have conducted various investigations and have found that a device employing the benzimidazolyl carbazole compound of the present invention as the host material of a light-emitting layer has a high luminous efficiency and can be driven by a low voltage.

In the organic light-emitting device utilizing phosphorescence of, for example, a phosphorescent Ir complex, the host material molecule is designed so that its lowest triplet energy is higher than that of the light-emitting material. By doing so, since the triplet excitation energy is confined by the light-emitting material in the light-emitting layer, a high luminous efficiency can be achieved.

However, in the blue phosphorescent device, the peak wavelength of the emission wavelength is in a short wavelength of 450 to 470 nm, and known host materials that can cope with such a high level of the lowest triplet energy are limited, and carbazole compounds are known as materials having the lowest high triplet energy at a high level.

Incidentally, in a light-emitting layer in which high-energy chemical species, such as holes, electrons, and excitons, are present at high densities, it is very important that the materials contained therein are chemically stable.

However, carbazole has a chemically highly active nitrogen-hydrogen bond and, therefore, cannot be used directly as a host material.

In addition, carbazole has a high hole-transporting property, but its electron-transporting property is not so as the hole-transporting property.

That is, there is a demand for a novel compound that can simultaneously achieve both high chemical stability and a high electron-transporting property, while maintaining the high triplet energy.

For solving the above-mentioned problems, the present inventors have conducted intensive studies and, as a result, have found that the benzimidazolyl carbazole compound of the present invention is useful as the host material of the phosphorescent device. The compound of the present invention is improved in the chemical stability and the electron-transporting property, while maintaining the high triplet energy as a carbazole compound.

In the benzimidazolyl carbazole compound of the present invention, the electron-transporting property has been improved by introducing benzimidazole into carbazole, compared to known phenyl group-substituted carbazole compounds.

Furthermore, in the benzimidazolyl carbazole compound according to the present invention, the bonding positions of benzimidazole and carbazole are characteristic.

It is known that the carbon-hydrogen bond between two nitrogen atoms of benzimidazole is chemically active.

Accordingly, in a novel molecular structure in which the nitrogen atom of carbazole is bonded to the carbon atom of the carbon-hydrogen bond of benzimidazole as shown by Formula [1], the chemically active sites are blocked with each other to give a chemically stable compound.

If benzimidazole and carbazole are bonded to each other at positions other than that shown in Formula [1], it is necessary to additionally introduce other substituents for blocking the highly active sites. However, an increase in the number of substituents generally causes a decrease in triplet energy and is therefore disadvantageous.

It is possible to bond the nitrogen atom to which $R^3$ is bonded in benzimidazole to the nitrogen atom of carbazole, but a nitrogen-nitrogen bond is chemically unstable compared to a nitrogen-carbon bond and is therefore disadvantageous.

It is known that 3-position and 6-position of carbazole are also chemically active to cause an electrochemical reaction, which may cause device degradation due to energization.

Since the benzimidazolyl carbazole compound of the present invention has substituents, $R_1$ and $R_2$, at the electrochemically active sites, 3-position and 6-position, respectively, electrochemical stability is obtained.

In addition, the substituent, $R_3$, is indispensable for obtaining the above-described chemical stability. In order to obtain high triplet energy, $R_3$ can be an alkyl group having 1 to 6 carbon atoms, in particular, a methyl group.

Furthermore, the introduction of $R_3$ causes steric repulsion between $R_3$ and the carbazole skeleton so that the benzimidazole skeleton is twisted with respect to the carbazole skeleton to decrease the planarity of the entire molecule. This has effects of preventing conjugation in the molecule from extending and of further increasing the triplet energy. Furthermore, the decrease in the planarity of the entire molecule can inhibit stacking, which is caused by molecular planarity, and intermolecular interaction with a phosphorescent material, resulting in prevention of an increase in emission wavelength and of a decrease in luminous efficiency.

It is possible to introduce a substituent to a hydrogen atom of the six-membered ring in benzimidazole, instead of $R_3$, but in such a case, steric repulsion with the carbazole ring is not generated. That is, the above-described effects cannot be expected, and a decrease in triplet energy due to an increase in the number of substituents is caused.

By the above-described effects, the benzimidazolyl carbazole compound of the present invention has high triplet energy and an excellent electron-transporting property and can thereby provide a satisfactory field for recombination of holes and electrons as a host material and can efficiently transport the triplet energy to the guest material. As a result, an organic light-emitting device having a high luminous efficiency and driven by a low voltage can be obtained.

The light-emitting material contained in the light-emitting layer may be a known material, but the light-emitting layer can contain a phosphorescent material as a guest material. Examples of the guest material include FIrpic, bis(3,5-difluoro-2-(2-pyridinyl)phenyl)tetrakis(1H-pyrazolyl)borate iridium (FIr6), and a phosphorescent Ir complex shown by a structural formula [Chem. 16] described below. Other examples of the guest material include fac-tris(2-(2-pyridinyl)phenyl)iridium ($Ir(ppy)_3$) and fac-tris(1-phenylisoquinoline)iridium ($Ir(piq)_3$). In the organic light-emitting device of the present invention, examples of the hole-transporting material contained in a hole-transporting layer include triarylamine derivatives, phenylenediamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, porphyrin derivatives, poly(vinylcarbazole), poly(silylene), and poly(thiophene).

Examples of the electron-transporting material contained in an electron-transporting layer include oxadiazole derivatives, oxazole derivatives, triazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organic metal complexes such as quinolinol aluminum complexes.

Examples of the structure of the organic light-emitting device according to the present invention include a structure in which anode/light-emitting layer/cathode disposed on a substrate in this order, a structure in which anode/hole-transporting layer/electron-transporting layer/cathode are disposed on a substrate in this order, a structure in which anode/hole-transporting layer/light-emitting layer/electron-transporting layer/cathode are disposed on a substrate in this order, a structure in which anode/hole-injecting layer/hole-transporting layer/light-emitting layer/electron-transporting layer/cathode are disposed on a substrate in this order, and a structure in which anode/hole-transporting layer/light-emitting layer/hole- and exciton-blocking layer/electron-transporting layer/cathode are disposed on a substrate in this order. Note that these five multilayered-type organic light-emitting devices are merely basic examples of the device structure and that the structure of the organic light-emitting device having the compound according to the present invention is not limited thereto. Various layer structures, for example, structures having an insulating layer at the interface between an electrode and an organic compound layer; an adhesion layer or an interference layer; or the electron-transporting layer or the hole-transporting layer constituted of two layers having different ionization potentials can be employed.

The hole-injecting material or the hole-transporting material can have a high hole mobility. Examples of low-molecular-weight or polymeric material having a hole-injecting property or a hole-transporting property include, but not limited to, triarylamine derivatives, phenylenediamine derivatives, stilbene derivatives, phthalocyanine derivatives, porphyrin derivatives, poly(vinylcarbazole), poly(thiophene), and other conductive polymers.

The electron-injecting material or the electron-transporting material is selected considering the balance with the hole mobility of the hole-injecting material or the hole-transporting material. Examples of the electron-injecting material or the electron-transporting material include, but not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

The anode material has a work function as large as possible, and examples thereof include simple metals such as gold, platinum, silver, copper, nickel, palladium, cobalt, selenium, vanadium, and tungsten; alloys of these metals; metal oxides such as tin oxide, zinc oxide, indium oxide, indium tin oxide (ITO), and indium zinc oxide; and conductive polymers such as poly(aniline), poly(pyrrole), and poly(thiophene). These electrode materials may be used alone or in combination. The anode may have a monolayer structure or a multilayer structure.

On the other hand, the cathode material has a work function as small as possible, and examples thereof include simple metals such as alkali metals (e.g., lithium), alkali earth metals (e.g., calcium), aluminum, titanium, manganese, silver, lead, and chromium; alloys of these simple metals, such as magnesium/silver, aluminum/lithium, and aluminum/magnesium; and metal oxides such as indium tin oxide (ITO). These electrode materials may be used alone or in combination. The cathode may have a monolayer structure or a multilayer structure.

In the organic light-emitting device according to the embodiment, the layer containing the organic compound according to the embodiment and the layer composed of another organic compound can be formed by various known methods. In general, these layers can be formed by vacuum deposition, ionic vapor deposition, sputtering, plasma, or known application (e.g., spin coating, dipping, casting, LB method, or ink jetting) of a solution of the compound dissolved in an appropriate solvent. The layer formed by vacuum deposition or application is low in, for example, crystallization and is therefore excellent in temporal stability. In a case of the application, a film can be also formed using a solution containing an appropriate binder resin.

Examples of the binder resin include, but not limited to, poly(vinylcarbazole) resins, poly carbonate resins, polyester resins, ABS resins, acrylic resins, polyimide resins, phenol resins, epoxy resins, silicone resins, and urea resins. These binder resins may be used alone as a homopolymer or a copolymer or in combination of two or more thereof. Furthermore, as necessary, known additives such as a plasticizer, an antioxidant, or a UV absorber may be used.

Use of Organic Light-Emitting Device

The organic light-emitting device according to the present invention can be used in display panels and lighting systems and also can be used in exposure light sources of image forming apparatuses of electrophotographic systems and back lights of liquid crystal display panels.

The display panel includes the organic light-emitting device according to the embodiment in the display portion. The display portion includes a plurality of pixels. The pixels each include an organic light-emitting device according to the embodiment and a thin-film transistor as an example of a switching device for controlling luminous brightness. The anode or the cathode of the organic light-emitting device is connected to the drain electrode or the source electrode of the thin-film transistor. The display panel can be used as an image display panel of, for example, a PC.

The display panel may be an image outputting apparatus having an image input portion inputting data from, for example, an area CCD, a linear CCD, or a memory card, and outputting the input image to the display portion. The display may include both an image-outputting function of displaying an image based on image data input from the outside, as a display portion of an imaging apparatus or an ink-jet printer, and an inputting function of inputting processed data of an image, as a control panel. The display panel may be used in the display portion of a multi-function printer.

A display panel employing the organic light-emitting device according to the embodiment will be described with reference to FIG. 1.

FIG. 1 is a schematic view illustrating a cross section of an organic light-emitting device according to the embodiment and a thin-film transistor as an example of the switching device connected to the organic light-emitting device. In this drawing, two pairs of the organic light-emitting device and the thin-film transistor are shown. The details of the structure will be described below.

In the display panel shown in FIG. 1, a moisture-proof film 2 for protecting a thin-film transistor or an organic compound layer is disposed on a substrate 1 of, for example, glass. The reference sign 3 indicates a metal gate electrode, the reference sign 4 indicates a gate-insulating film, and the reference sign 5 indicates a semiconductor layer.

The thin-film transistor 8 includes a semiconductor 5, a drain electrode 6, and a source electrode 7. An insulating film 9 is disposed at the upper portion of the thin-film transistor 8, and an anode 11 of the organic light-emitting device is connected to the source electrode 7 through a contact hole 10. The display panel is not limited to this structure as long as one of the anode and the cathode is connected to either the source electrode or the drain electrode of the thin-film transistor.

In this drawing, the organic compound layer 12 is simplified and drawn as one layer, but is actually composed of a plurality of organic compound layers. A first protection layer 14 and a second protection layer 15 are disposed on a cathode 13 for inhibiting degradation of the organic light-emitting device.

In the display panel according to the embodiment, the switching device is not particularly limited and may be a thin-film transistor employing single crystal silicon, an MIM device, or an amorphous silicon device.

EXAMPLES

The present invention will be described in detail with reference to examples below, but is not limited thereto.

Example 1

Synthesis of Exemplary Compound H-08

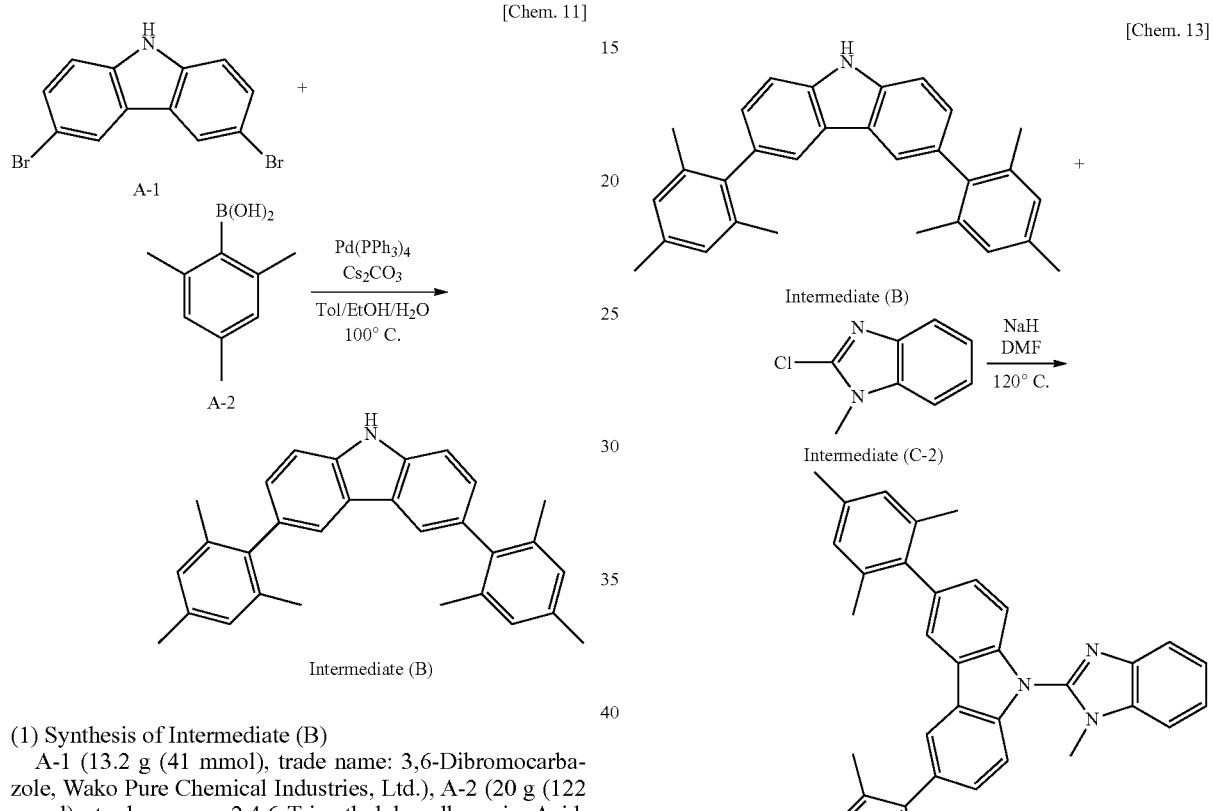

(1) Synthesis of Intermediate (B)

A-1 (13.2 g (41 mmol), trade name: 3,6-Dibromocarbazole, Wako Pure Chemical Industries, Ltd.), A-2 (20 g (122 mmol), trade name: 2,4,6-Trimethylphenylboronic Acid, Wako Pure Chemical Industries, Ltd.), Pd(PPh$_3$)$_4$ (0.938 g (0.8 mmol)), Cs$_2$CO$_3$ (40 g (123 mmol)), toluene (150 mL), ethanol (100 mL), and water (100 mL) were placed in a 500-mL flask, followed by stirring at 100° C. for 8 hours. The reaction solution was cooled to room temperature, and the organic layer was extracted and concentrated. The resulting residue was purified by a column (developing solvent: ethyl acetate/heptane=1/4) to obtain 9.8 g (24 mmol) of an intermediate (B). The yield was 60%.

(2) Synthesis of Intermediate (C-2)

2-Chloro-benzimidazole (20 g (131 mmol, trade name: 2-Chlorobenzimidazole, manufactured by Aldrich) and THF (150 mL) were placed in a 500-mL three-neck flask, and t-butoxy sodium (13.8 g (144 mmol)) was added thereto under ice cooling. The mixture was stirred at room temperature for 1 hour. Subsequently, a solution of methyl iodide (24.2 g (170 mmol)) and THF (30 mL) was dropped into the flask under ice cooling, and the resulting mixture was stirred at room temperature for 5 hours. The reaction solution was extracted with chloroform, followed by drying over anhydrous sodium sulfate. Subsequently, the solvent was removed to obtain 18.6 g (yield: 85%) of an intermediate (C-2) (2-chloro-1-methyl-1H-benzimidazole, white crystal).

(3) Synthesis of Exemplary Compound H-08

The intermediate (B) (1.32 g (3.3 mmol)), DMF (50 mL), and NaH (60 wt %, 0.130 g (3.3 mmol)) were placed in a 100-mL flask in this order. The mixture was stirred at room temperature for 20 minutes, followed by addition of the intermediate (C-2) (0.54 g (3.3 mmol)) thereto. Subsequently, the resulting mixture was stirred at 120° C. for 8 hours, and water (50 mL) was added to the mixture to terminate the reaction, followed by washing with water and suction filtration. The resulting residue was purified by a column (developing solvent: chloroform/heptane=1/1), followed by dispersion washing with methanol. Furthermore, the resulting powder was dried and was purified by sublimation (10$^{-4}$ Pa, 300° C.) to obtain 0.26 g (0.5 mmol) of an exemplary compound (H-08). The yield was 15%.

NMR (CDCl$_3$); δ 7.9 (1H), δ 7.8 (2H), δ 7.5 (1H), δ 7.4-7.5 (4H), δ 7.2 (2H), δ 7.0 (4H), δ 3.8 (3H), δ 2.4 (6H), δ 2.0 (6H), δ 2.0 (6H).

MALDI-MS; 533.3.

Example 2

The 0-0 band (triplet energy level) of phosphorescence at 77 K of a toluene solution (concentration: $10^{-3}$ mol/L) of the synthesized exemplary compound H-08 of the present invention was measured with a spectrophotofluorometer (manufactured by Hitachi, Ltd., model No. F-4500) to be 417 nm.

Example 3

Production of Organic Light-emitting Device

Synthesis of Compound E-01

[Chem. 14]

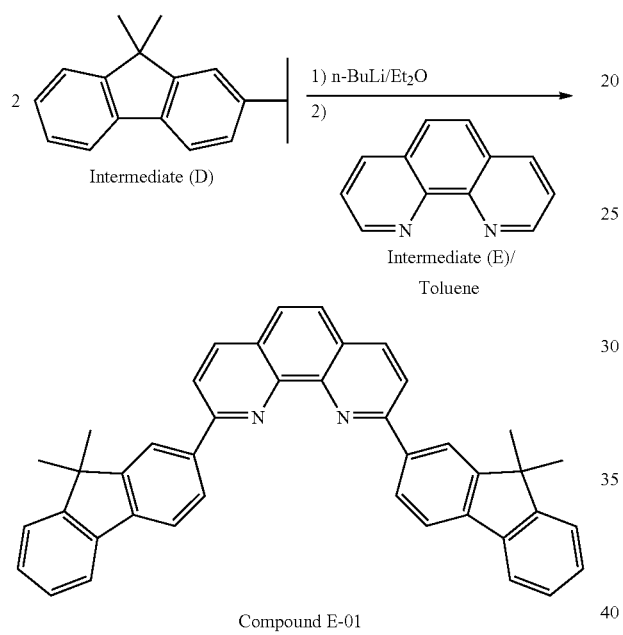

Compound E-01

2-Iodo-9,9-dimethylfluorene (intermediate (D), 5.8 g (18.1 mmol)) and diethyl ether (80 mL) were placed in a 300-mL three-neck flask, and n-butyllithium (15 wt % hexane solution, 11.7 mL (18.1 mmol)) was dropped into the flask with stirring at −78° C. in a nitrogen atmosphere. The resulting mixture was warmed to room temperature and was stirred for 1 hour, and then cooled to −20° C. Phenanthroline (intermediate (E), 0.81 g (4.51 mmol) dispersed in toluene (100 mL) was dropped into the mixture. The resulting mixture was stirred at room temperature for 12 hours, followed by addition of water. The organic layer was extracted with chloroform, dried over anhydrous sodium sulfate, and purified by an alumina column (developing solvent: a mixture of hexane and chloroform) to obtain 2.04 g (yield: 80%) of a compound E-01 (white crystal).

Production of Device

A film of indium tin oxide (ITO) having a thickness of 120 nm was formed as an anode on a glass substrate by sputtering. The formed ITO film was patterned so as to have an opposing electrode area of 4 mm². The resulting product was subjected to ultrasonic washing in ultrapure water and then in isopropyl alcohol (IPA) and was further subjected to UV/ozone washing to obtain a transparent and conductive supporting substrate.

Then, as a hole-injecting material, a chloroform solution containing 0.1 wt % of a known hole-transporting material (trade name: 4,4',4''-Tris(carbazol-9-yl)triphenylamine (TCTA), Luminescence Technology (Taiwan)) shown by the following structural formula [Chem. 15] was prepared. This solution was dropped onto the ITO electrode prepared above and spin-coated at 1000 rpm for 60 seconds to form a film with a thickness of 30 nm. Then, the solvent in the thin film was completely removed by drying in a vacuum oven at 80° C. for 10 minutes to form a hole-injecting layer.

Then, the above-mentioned TCTA was vapor-deposited on the hole-injecting layer to form a hole-transporting layer with a thickness of 20 nm. Thus, hole-injecting/transporting layer was formed.

[Chem. 15]

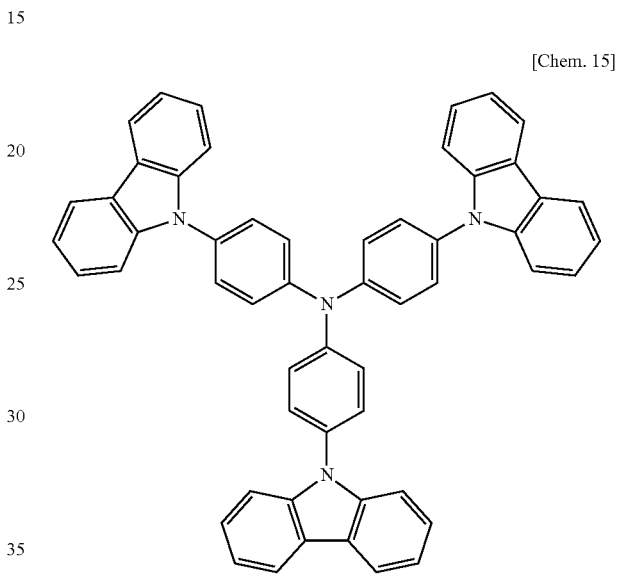

Then, the exemplary compound H-08 of the benzimidazolyl carbazole compound of the present invention and a phosphorescent Ir complex shown by the following structural formula [Chem. 16] were co-deposited on the hole-transporting layer at deposition rates so that the concentration of the phosphorescent Ir complex is 10 wt % to form a light-emitting layer with a thickness of 40 nm. The film was formed under vapor deposition conditions of a degree of vacuum of $2.0 \times 10^{-5}$ Pa.

[Chem. 16]

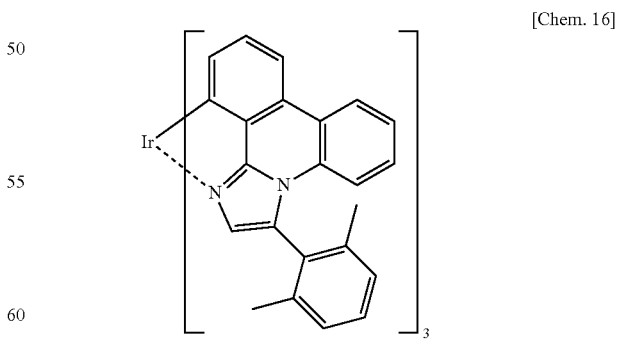

Furthermore, the compound E-01 was vapor-deposited on the light-emitting layer to form an electron-injecting/transporting layer with a thickness of 30 nm. The degree of vacuum during the vapor deposition was $2.0 \times 10^{-5}$ Pa, and the deposition rate was 0.1 nm/sec.

Then, as a cathode, a lithium fluoride (LiF) film with a thickness of 0.5 nm and an aluminum (Al) film with a thickness of 120 nm were vapor-deposited. The degree of vacuum during the vapor deposition was $4.0 \times 10^{-5}$ Pa, and the deposition rates of lithium fluoride (LiF) and aluminum (Al) were 0.015 nm/sec and 0.4 to 0.5 nm/sec, respectively.

The resulting organic light-emitting device was covered with a protection glass plate in a dried air atmosphere and was sealed with an epoxy resin adhesive, not to cause device degradation due to absorption of moisture.

Device Evaluation

A voltage was applied to the thus-obtained device using the ITO electrode as a positive electrode and the LiF/Al electrode as a negative electrode. As a result, when the luminous brightness was 500 cd/m$^2$, the applied voltage was 11.2 V, and blue luminescence with a luminous efficiency of 4.2 lm/W was observed.

Comparative Example

A device was produced as in Example 3 except that a comparative compound R-01 shown by the following structural formula [Chem. 17] described in PTL 1 was used instead of the compound H-08 in Example 1, and was similarly evaluated. When the luminous brightness was 500 cd/m$^2$, the applied voltage was 13.8 V, which was higher than that in the case of the compound H-08. Furthermore, blue luminescence was observed as in the case of the compound H-08, but the luminous efficiency was 3.0 lm/W, which was lower than that in the case of the compound H-08.

[Chem. 17]

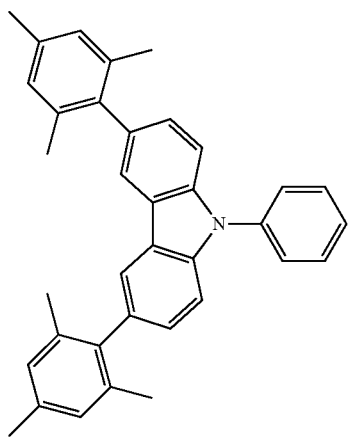

R-01

It was shown by the results above that a high luminous efficiency and driving at a low voltage can be achieved by using the benzimidazolyl carbazole compound of the present invention as a material for an organic light-emitting device.

While the present invention has been described with reference to an exemplary embodiment, it is to be understood that the invention is not limited to the disclosed exemplary embodiment. The scope of the following claims is to be accorded the broadest interpretation so as to encompass all such modifications and equivalent structures and functions.

This application claims the benefit of Japanese Patent Application No. 2010-082828, filed Mar. 31, 2010, which is hereby incorporated by reference herein in its entirety.

INDUSTRIAL APPLICABILITY

The technology of the present invention can be applied to not only display panels such as full color displays but also, for example, lighting instruments, instruments having photoelectric conversion devices, and electrophotographic machines.

The invention claimed is:

1. A benzimidazolyl carbazole compound shown by the following Formula [1]:

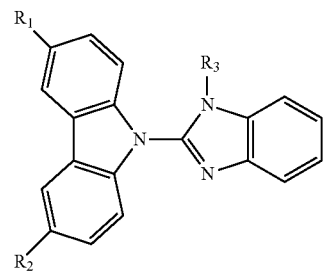

[1]

in the formula, $R_1$ and $R_2$ each independently represent an unsubstituted phenyl group or a substituted phenyl group substituted with at least one alkyl group having 1 to 6 carbon atoms; and $R_3$ represents an alkyl group having 1 to 6 carbon atoms.

2. The compound according to claim 1, wherein $R_1$ and $R_2$ each independently represent a tolyl group, a xylyl group, or a mesityl group.

3. An organic light-emitting device comprising at least one organic layer disposed between a pair of electrodes opposing each other, wherein the at least one organic layer comprises a light-emitting layer comprising the compound according to claim 1.

4. The organic light-emitting device according to claim 3, wherein the light-emitting layer comprises a phosphorescent Ir complex as a guest material.

5. An image display panel comprising the organic light-emitting devices according to claim 3 and thin-film transistors.

6. An image display panel comprising the organic light-emitting elements according to claim 4 and thin-film transistors.

7. An image display panel comprising the organic light-emitting elements according to claim 3 and switching element.

8. An image display panel comprising the organic light-emitting elements according to claim 4 and switching element.

* * * * *